(12) United States Patent
Taljaard (10) Patent No.: US 8,974,382 B2
(45) Date of Patent: Mar. 10, 2015

(54) MEDICAL TUBE RETAINING DEVICE

(75) Inventor: André Johan Taljaard, Kroonstad (ZA)

(73) Assignee: Jirehsa Medical (Proprietary) Limited, River Club (ZA)

( * ) Notice: Subject to any disclaimer, the term of this patent is extended or adjusted under 35 U.S.C. 154(b) by 1693 days.

(21) Appl. No.: 10/520,231

(22) PCT Filed: May 27, 2003

(86) PCT No.: PCT/ZA03/00068
§ 371 (c)(1),
(2), (4) Date: Jan. 4, 2005

(87) PCT Pub. No.: WO2004/007009
PCT Pub. Date: Jan. 22, 2004

(65) Prior Publication Data
US 2005/0252514 A1    Nov. 17, 2005

(30) Foreign Application Priority Data
Jul. 5, 2002    (ZA) .................................. 2002/5373

(51) Int. Cl.
*A61B 1/32*    (2006.01)
*A61M 16/04*    (2006.01)
*A61M 25/02*    (2006.01)

(52) U.S. Cl.
CPC ..... *A61M 16/0488* (2013.01); *A61M 2025/022* (2013.01); *A61M 16/0493* (2014.02)
USPC ....................... 600/238; 433/140; 128/200.26

(58) Field of Classification Search
CPC ..................... A61M 16/0488; A61M 16/0493; A61M 16/0497; A61M 2025/022
USPC ......... 600/195, 237, 238, 239, 241, 114, 120; 433/93, 140; 128/200.26, 207.14
See application file for complete search history.

(56) References Cited

U.S. PATENT DOCUMENTS

| | | | |
|---|---|---|---|
| 1,094,575 A * | 4/1914 | Joutras | 600/219 |
| 1,389,436 A | 8/1921 | Cameron | |
| 3,772,790 A | 11/1973 | Swan-Gett et al. | |
| 4,053,984 A * | 10/1977 | Moss | 433/93 |
| 4,495,945 A | 1/1985 | Liegner | |
| 4,793,327 A | 12/1988 | Frankel | |
| 4,898,535 A * | 2/1990 | Bergersen | 433/6 |
| 5,626,128 A | 5/1997 | Bradley et al. | |
| 5,769,635 A * | 6/1998 | Eldreth | 433/93 |
| 5,941,246 A | 8/1999 | Roopchand | |
| 6,209,542 B1 | 4/2001 | Thornton | |
| 6,702,739 B2 | 3/2004 | Levisman | |
| 6,755,191 B2 * | 6/2004 | Bertoch et al. | 128/200.26 |
| 6,805,127 B1 * | 10/2004 | Karasic | 128/861 |

FOREIGN PATENT DOCUMENTS

WO    WO 96/11029 A    4/1996

* cited by examiner

*Primary Examiner* — Cris L Rodriguez
*Assistant Examiner* — Hao D Mai
(74) *Attorney, Agent, or Firm* — Frommer Lawrence & Haug LLP; Ronald R. Santucci (57) ABSTRACT

A new medical tube guiding device, the device including a first patient engaging portion configured to engage a zone of an upper jaw of the patient and a second patient engaging portion configured to engage a zone of a lower jaw of the patient. The first and second patient engaging zones are biased apart to provide a working gap between them. The invention also provides for a guide means for a medical tube that is supportable on one or both of the patient engaging portions and locatable relative to the patient engaging portions to guide the medical tube through the working gap into a mouth of the patient.

12 Claims, 5 Drawing Sheets

MEDICAL TUBE RETAINING DEVICE

This application is a 371 of PCT/ZA2003/000068 filed on May 27, 2003, published on Jan. 22, 2004 under publication number WO 2004/007009 A1 which claims priority benefits from South African Patent Application Number 2002/5373 filed Jul. 5, 2002.

FIELD OF THE INVENTION

This invention relates to a medical tube retaining device for holding a medical tube such as an endotracheal tube.

BACKGROUND

Tubes are employed for many purposes to provide for passage of air or fluids, including gases, to and from the human body. One type of tube is an endotracheal tube, which is adapted to be inserted through the oral cavity of a patient and into the trachea to provide for the supply of fluids or gasses to the body, for the monitoring of internal conditions in the body and to provide for removal of secretions from within the body.

It is desirable to secure the endotracheal tube in place within the patient to prevent it from being inadvertently advanced into the left or right tracheal bifurcation or retracted from the trachea after it has been properly positioned. However, it is difficult to properly secure an endotracheal tube to a patient's oral cavity to prevent these events.

Presently, adhesives are used to keep the tube positioned which are ineffective because of the presence of facial hair, oily skin, dirt, blood, etc. According to this approach of retaining a medical tube near the tube insertion site, one or more adhesive strips are applied directly over the tube and to the skin of the patient. In order to adjust the position of the tube, the adhesive strip must be removed from the skin and then reapplied in the desired location. This significantly weakens the holding strength of the adhesive, and often requires the placement of additional strips on the tube and skin to properly anchor the tube. Natural body secretions further reduce the ability of the strip to properly retain the tube.

Another problem is that the endotracheal tube is usually relatively easy to deform and passes between the patient's teeth if inserted orally. It is desirable to prevent the lumen of the endotracheal tube from being obstructed by a patient's teeth when the patient attempts to bite clown during or with extubation after reversal of the muscle relaxant. Obstruction of the endotracheal tube can lead to, for example, hypoxia, or other similar conditions.

The above approaches are ineffective in protecting against possible obstruction of the tube. Bite blocks can be effective in keeping a patient's jaw open and thus prevent the teeth from clamping down on the endotracheal tube. The problem is that the bite block is yet another piece of equipment that may be inserted into the patient's mouth along with other medical apparatuses.

Other prior art devices using a clamp attached to an adhesive strip are likewise ineffective. These devices are generally applicable only for a single, specific tube size and do not effectively restrict sliding movement of the tube within the clamp.

Notwithstanding the present methods and ways, a need still exists for a better way to secure an endotracheal tube in a patient while avoiding the above stated problems.

SUMMARY OF THE INVENTION

According to one aspect of the present invention, a medical tube retaining device for an airway includes:

first and second spaced-apart arm portions;
a base portion from which the arms are radially spaced; and
a clamp portion mounted on the base portion for engaging and holding the tube,
said spaced-apart arm portions meeting at the base portion to permit displacement thereof between an engaged and disengaged position.

The clamp may be adjustable for accommodating different size tubes.

Alternatively, a medical tube retaining device for an airway may include:

first and second spaced-apart arm portions;
a biasing means for biasing said arm portions apart; and
at least one clamp portion for engaging and holding the tube.

The biasing means may be a coil spring which urges said spaced-apart arm portions and dental arches away from each other.

The invention may further include first and second retaining extensions complementally shaped to fit the upper and lower teeth of a patient, said extensions being located at distal ends of the first and second spaced-apart arms.

Said retaining extensions may include a flange and slip-resistant inner lining for frictionally engaging with the teeth of a patient.

The retaining extensions may be in the form of a dental arch.

The device may be provided with adjustment means for the retaining extensions including complementary locking teeth formed on each of the arms.

The locking teeth have respective engaging surfaces to provide locking adjustment of the retaining extensions.

Alternatively, the distal ends of the first and second spaced-apart arms may be fixed in position.

According to one embodiment of the invention, the said spaced-apart arm portions comprise a suitable recoil material for movement between an engaged and disengaged position. Typically the recoil material would be a resiliently deformable material.

According to another embodiment of the invention, the clamp includes a slip-resistant inner lining for frictionally engaging the tube.

According to yet another embodiment of the invention, the slip-resistant inner lining is formed of rubber or plastic.

According to yet another embodiment of the invention, the first and second retaining extensions are formed on the spaced-apart arms, to facilitate engagement of the retaining extensions with the teeth of a patient.

Therefore, the present invention provides a medical tube retaining device for an endotracheal tube that can secure the tube to the teeth of a patient but at the same time permits the position of the endotracheal tube with respect to the patient to be readily adjusted by a medical professional.

The present invention also preferably provides a retaining device that prevents obstruction of an endotracheal tube by a patient's teeth.

A retaining device according to the present invention may be used with any type of endotracheal tube, which needs to be inserted into a patient's airway via the mouth, such as a respiratory tube.

The inventor believes the advantages of the invention are that it securely holds an endotracheal tube at a constant depth within the patient once set, prevents the obstruction of an inserted endotracheal tube in a patient, easy to use during the initial insertion of an endotracheal tube with adjustment of the depth within the patient of the endotracheal tube, and the removal of the endotracheal tube provides space for the insertion of additional medical instruments into the patient's mouth, can be used even when debris, blood, facial hair, dirt, perspiration and excessive soft tissue are present in the vicinity, endotracheal tube is protected from obstruction resulting from forces being applied to it by the patient's jaw and teeth, and the minimization and elimination of the likelihood of inadvertent extubation or mainstem intubation.

According to an aspect of the invention, there is provided a medical tube retaining device, the device including:

a first patient engaging portion configured to engage a zone of an upper jaw of a patient;

a second patient engaging portion configured to engage a zone of a lower jaw of the patient, said first and second patient engaging portions being biased apart to provide a working gap between them; and a medical tube guide means supportable on one or both of the patient engaging portions and locatable relative to the patient engaging portions to guide the medical tube through the working gap into the mouth of the patient.

The first and second patient engaging portions may be portions of a body having resiliently deformable portions.

The first and second patient engaging portions may be in the form of a pair of arms having tooth engaging portions.

The first and second patient engaging portions are in the form of a pair of dental arches having tooth engaging portions.

The medical tube guide means may be sized to permit a view into the mouth of the patient through the working gap when the medical tube is in place in the mouth of the patient.

The medical tube guide means may be located eccentrically the working gap.

The medical tube guide means may be configured to immobilize the medical tube in a desired position.

The medical tube guide means may include securing means operable between a securing and a releasing position, said securing means being configured to secure the medical tube against longitudinal displacement unless the securing means is in the releasing position in which case the medical tube is longitudinally displaceable into and out of the mouth of the patient.

The pair of arms may meet at an apex, which apex forms a support point for the medical tube guide means.

The pair of arms may be pivotally displaceable relative to each other.

The first and second patient engaging portions may be biased apart by one or more of resilient deformability of the material, a coil spring, a leaf spring, and fluid pressure.

The medical tube guide means may include a eye through which the medical tube is to be guided passes.

The medical tube guide means may include a slip resistant portion to inhibit the free movement of the medical tube through the medical tube guide means.

The first and second patient engaging portions may include portions configured to approximate the bite size and dimensions of the patient.

The medical tube retaining device may include two or more medical tube guide means.

It is to be appreciated from this specification that the device as described herein may be proportioned to accommodate a smaller child's mouth, as well as a person who no longer has their own teeth.

DETAILED DESCRIPTION OF THE DRAWINGS

The invention will now be described, by way of non-limiting example, with reference to the accompanying diagrammatic drawings wherein.

In the accompanying drawings, reference numeral 10 generally refers to a medical tube retaining device and reference numeral 12 to a medical tube, be it an endotracheal, gastric or endoscopic tube.

Figure 1:
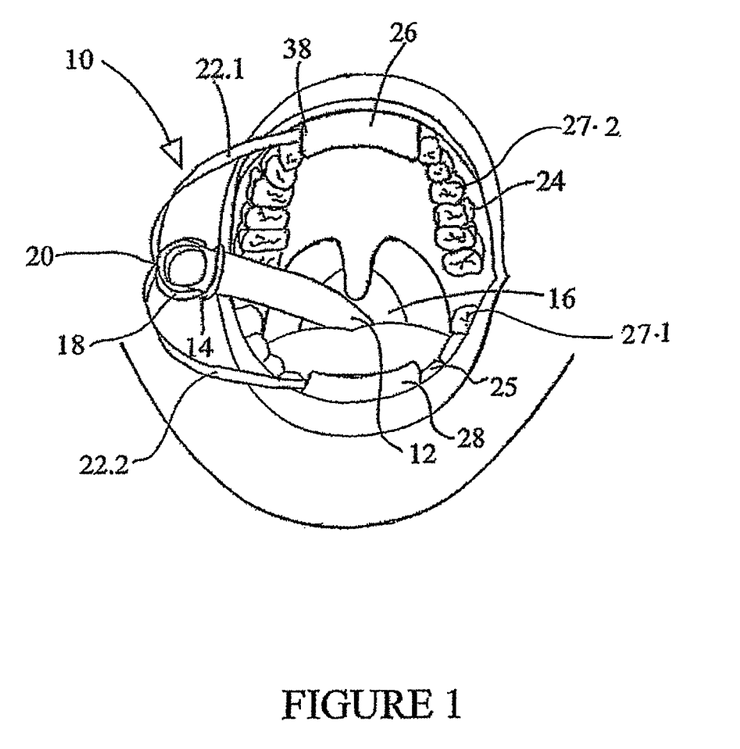
FIG. 1 is a view of one embodiment of a medical tube retaining device when in use with an intubated patient.
Figure 2:
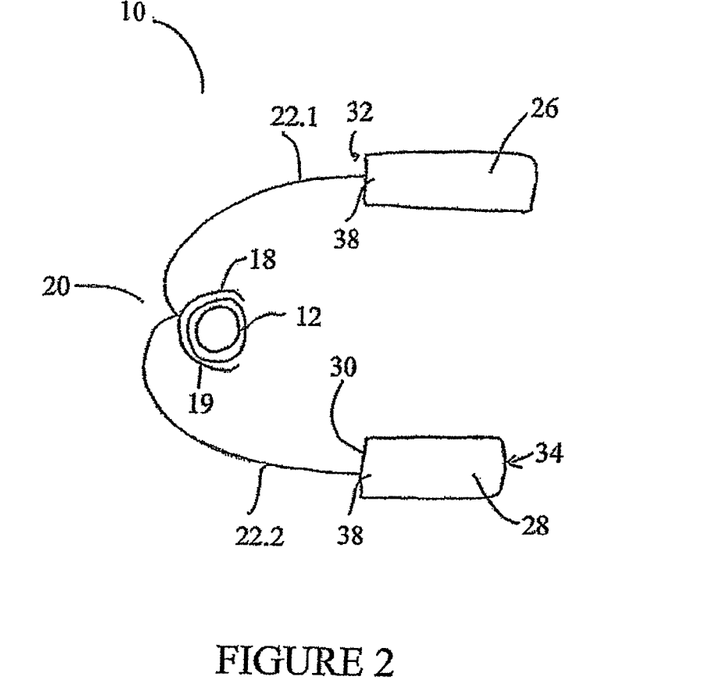
FIG. 2 is a plan view of an embodiment of a medical tube retaining device.

In one embodiment, a clamp 14 is attached to the medical tube retaining device 10 for holding the tube 12 as it exits the airway 16 of a patient. The clamp 14 may be integrally formed from a molded plastic material, and includes a mounting clip 18 attached to a base 20 formed by the joint of a pair of spaced-apart arms 22. The spring loaded arms 22.1 and 22.2 are connected together at a connecting base 20. The arms 22.1 and 22.2 are movable between an engaged position with the upper and lower jaw of the patient as shown in FIG. 1 and a disengaged position when not in use as shown in FIG. 2.

The spaced apart arms 22 may be in the form of dental arches 112 and 114.

Alternatively, clamp 14 in the form of a suitable fastening means (not shown) is attached to the clip 18 for holding the tube 12 as it exits the airway 16 of the patient. The fastening means encircles the tube 12 accordingly whereby it may be attached to the base 20. Said base 20 is in fixed arrangement with one or more of the dental arches 112 and 114 or spaced apart arms 22.

In another embodiment, the spring loaded arms 22.1 and 22.2 may form at least one spring loaded coil (not shown). The arms 22.1 and 22.2 are movable between an engaged and a disengaged position. Ideally, the spring loaded coil is positioned to force the upper and lower dental arches apart to maintain the jaws of a patient in an open position. It is to be appreciated that a secondary spring loaded coil may also be positioned to enhance the force applied to the upper and lower dental arches. Typically in this embodiment the retaining device 10 includes first and second spaced-apart arms 22.1 and 22.2, spaced radially from the coil. A clip 18 and clamp 14 may be mounted on base 20 for engaging and holding the tube 12. The base 20 may be fixed to dental arch 24 or any other suitable position to retain the tube 12 in a fixed location. The spaced-apart arms 22.1 and 22.2 may also be jointed at the base 20 for movement between an engaged and disengaged position.

Figure 3:
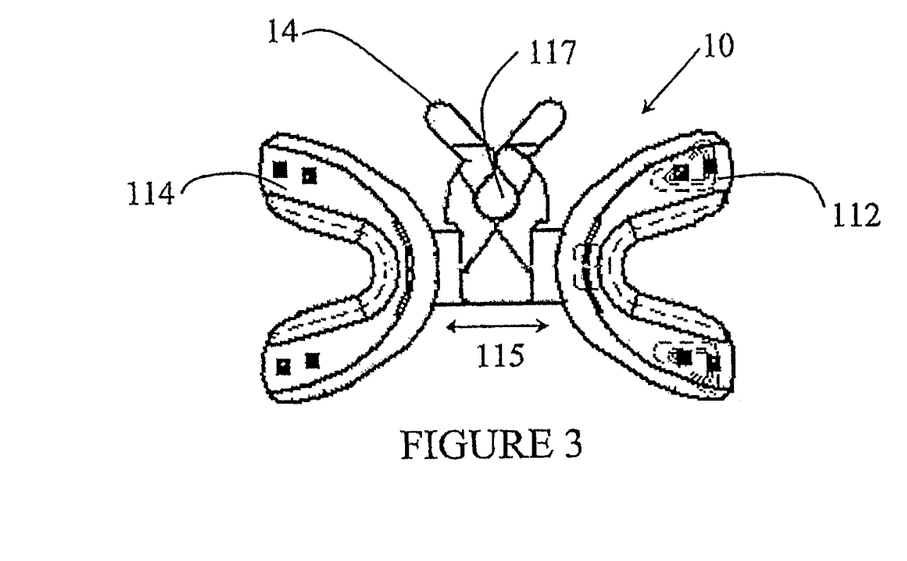
FIG. 3 is a plan view of an embodiment of the medical tube retaining device.
Figure 4:
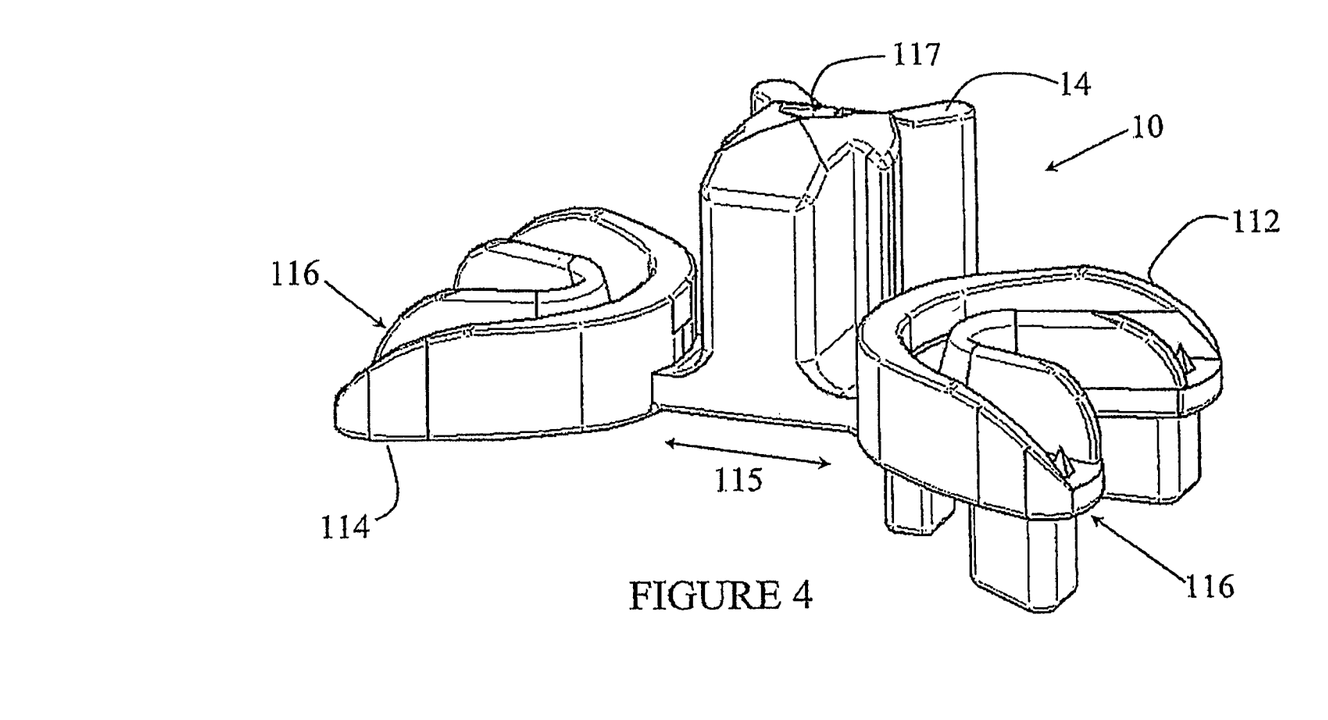
FIG. 4 is an isometric view of the medical tube retaining device.
Figure 5:
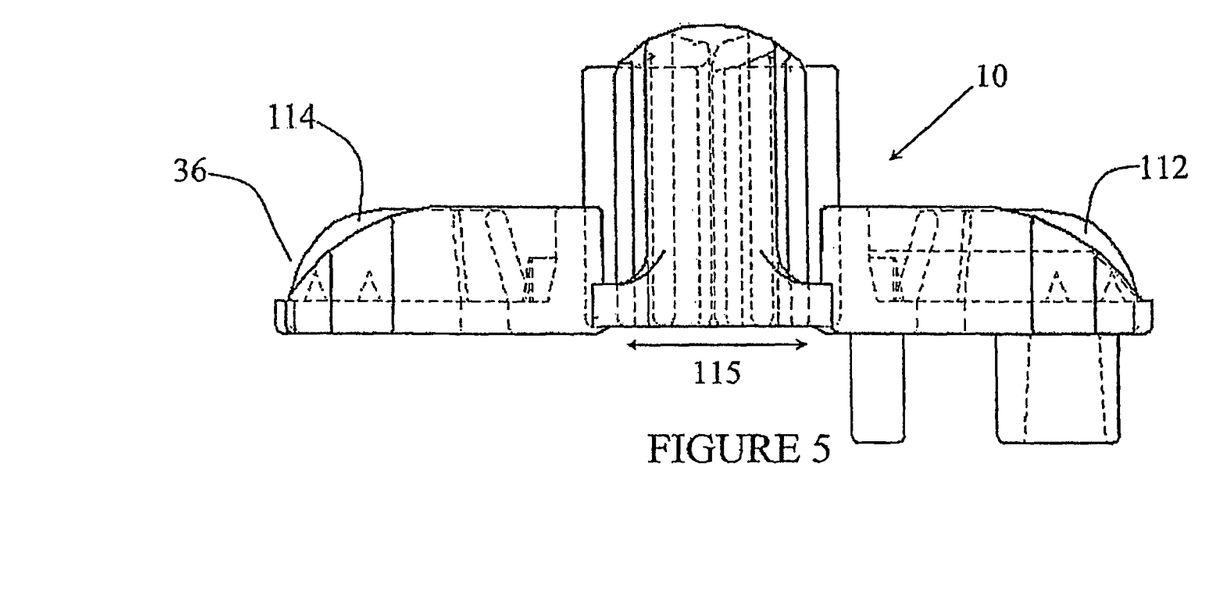
FIG. 5 is a side view of the medical tube retaining device.

In another embodiment, the medical retaining device includes first and second retaining extensions 26 and 28 complementally shaped to fit onto the upper teeth and lower teeth 27.1 and 27.2 of a patient, attached to the distal end 30 of the first and second spaced-apart arms 22.1 and 22.2. Said retaining extensions 26 and 28 may include a flange 32 and slip-resistant inner lining 34 for frictionally engaging with the teeth 27.1 and 27.2 of a patient (not shown). In another embodiment, the extensions are in the form of dental arches 36 (FIGS. 3 to 5)

An adjustment means 38 for the retaining extensions 26 and 28 may include complementary locking teeth (not shown) formed on each of the arms 22.1 and 22.2 The locking teeth (not shown) have respective engaging surfaces (not shown) to provide locking adjustment of the retaining extensions 26 and 28.

The present invention provides a medical tube retaining device 10 for an endotracheal tube 12 that can secure the tube 12 to the teeth 27.1 and 27.2 of a patient, but at the same time permits the position of the endotracheal tube 12 with respect to the patient to be readily adjusted.

In an embodiment, the retaining extension 26 is positioned and forced over the upper teeth 27.1 of a patient. Similarly, the retaining extension 28 is positioned over the lower teeth 27.2 to set the retaining device 10 in an engaged position. The spaced-apart arms 22.1 and 22.2 (preferably spring-loaded) extend from the retaining extensions 26 and 28, respectively to form a joint at base 20. Seated upon said base 20, are a clip 18 and clamp 14 having an opening 40 for receiving an endotracheal tube 12, such as a respiratory tube.

In an alternative embodiment, one of the dental arches 36 are positioned and forced over the upper teeth 27.1 of a patient. Similarly, the lower dental arch 36 is positioned over the lower teeth 27.2 to set the retaining device 10 in an engaged position. The spaced-apart arms 22.1 and 22.2 (preferably spring-loaded) extend from the dental arches 36, respectively to form a pivotal joint at a coil (not shown). Likewise, a secondary set of spaced apart arms may extend from the dental arches 36 to form a pivotal joint at another coil (not shown).

Not shown in the drawings is a fastening means which is attached to the base for releasably restraining the endotracheal tube with respect to the spaced-apart dental arches. The spring loaded coils apply a force onto the patient's dental arches 24 and 25, to remain in a spaced apart relationship accordingly whereby the retaining device 10 may perform the function of a bite block (not shown) by keeping the jaws of a patient in an open position.

Alternatively, extensions 26 and 28 may extend further towards each other for protecting the endotracheal tube 12 passing through the retaining device 10 from obstruction by a patient's teeth 27.1 and 27.2.

The retaining extensions 26 and 28 can be any member having outer dimensions complementally shaped and large enough to grip onto the teeth 27.1 and 27.2 of a patient. Thus, preventing the endotracheal tube 12 to which the retaining extensions 26 and 28 are attached, from being inadvertently advanced into the patient's mouth after it has been properly positioned in the patient's airway 16. The shape of the retaining extensions 26 and 28 is critical. The retaining extensions 26 and 28, preferably is each a plate like member having a flange 32 with a thickness that is small relative to its length and height. The retaining extensions 26 and 28, preferably has a channeled bend in a dental-arch-shape, forming a front and back wall for gripping therein the teeth 27.1 and 27.2 of a patient and if necessary, the surrounds of the bases of the teeth 27.1 and 27.2.

In one embodiment, the spaced-apart arms 22.1 and 22.2 extend from the retaining extensions 26 and 28 to form a joint at the base 20. A clip 18 is seated upon base 20 with an opening 19 for receiving the endotracheal tube 12 through the opening 19. The opening 19 preferably has a diameter that is sufficiently large that the endotracheal tube 12 can easily pass through it. More preferably, the opening 19 allows the position of the endotracheal tube 12 with respect to the spaced-apart arms 22.1 and 22.2 and retaining extensions 26 and 28 to be adjusted without the exertion of much force. For example, the endotracheal tube 12 may fit loosely inside the opening 19.

In an alternative embodiment, a medical tube retaining device 10 for an airway 16 may comprise first and second spaced-apart arms 22.1 and 22.2, spaced radially from at least one spring loaded coil (not shown), and at least one clip mounted on a base for engaging and holding the tube (not shown). Said spaced-apart arms are positioned to force a set of dental arches away from each other for movement between an engaged and disengaged position.

The fastening means (not shown) secured to the base (not shown), is used to releasably secure the endotracheal tube 12 to the clip (not shown). Preferably when the fastening means is open, the attached endotracheal tube 12 can freely move in its longitudinal direction with respect to the clip to enable the depth in the patient of the endotracheal tube 12 to be adjusted. Preferably when fastening means is closed, the fastening means engages the endotracheal tube 12 sufficiently tight to resist movement of the endotracheal tube 12 in its longitudinal direction with respect to the clip without obstructing the endotracheal tube 12. This function of the fastening means can be accomplished by a variety of structures.

Alternatively, the fastening means may be in the form of a clamp 14. The clamp 14 may have a closed position, and an open position. Preferably when the clamp 14 is open, the attached endotracheal tube 12 can freely move in its longitudinal direction with respect to the spaced-apart arms 22 to enable the depth in the patient of the endotracheal tube 12 to be adjusted. Preferably when the clamp 14 is closed, the clamp 14 engages the endotracheal tube 12 sufficiently tight to resist movement of the endotracheal tube 12 in its longitudinal direction with respect to the spaced-apart arms 22 without obstructing the endotracheal tube 12. This function of the clamp 14 can be accomplished by a variety of structures.

The clamp 14 is not restricted to one having pivotal jaws. For example, it may have jaws that translate rather than rotate with respect to each other to open and close the clamp 14. Alternatively, the clamp 14 may be replaced with a noose mechanism.

It should be appreciated that when the retaining device 10 is engaged, the first retaining extension 26 exerts a force in the direction of the upper teeth 27.1 due to the spring-loaded arm 22.1 and coil, while the second retaining extension 28 exerts a force in the opposite direction towards the lower teeth 27.2 of the patient due to spring-loaded arm 22.2 and coil, accordingly whereby the jaws of the patient are forced open. In this engaged position, the retaining device 10 can prevent the patient from obstructing the endotracheal tube 12 passing through the clip 18 and clamp 14.

In an alternative embodiment, the retaining extensions 26 and 28 may form a biting block where opposing sides of the extensions 26 and 28 may be forced onto each other by the jaws of the patient and thus preventing the biting of the endotracheal tube 12 since the patient's teeth 27.1 and 27.2 will typically be able to exert a force on the extensions 26 and 28. The illustrated retaining extensions 26 and 28 may each have an enlarged portion such as an annular flange (not shown) to help retain the patient's incisors in the retaining extensions 26 and 28.

A further alternative embodiment includes additional clips and clamps to hold a second endotracheal tube. This additional clamp may be incorporated into clamp 14 by providing a second hump to form a second opening. Alternatively, the additional clamp may be a separate clamp identical to clamp 14.

The retaining device 10 may be made of a variety of materials, including both metals and plastics. It may be convenient if the retaining extensions 26 and 28 are made of a see-through material, such as a transparent plastic, to enable a patient's mouth to be readily observed during use of the retaining device to check for obstructions or contamination. The different components of the retaining device may be separately formed and then secured to each other, or a plurality of the components may be integrally formed with one another.

In the embodiments, the retaining extensions 26 and 28 and spaced apart arms 22 are integrally formed with one another preferably using a plastic molding process. It should be appreciated that the spaced-apart arms 22 may be slidingly adjustable with reference to each other. Depending upon the materials of which these components are made, it is also possible to integrally form the clip 18 and clamp 14 with the dental arches 26 and 28 or spaced-apart arms 22.

When the distal end has been properly positioned, the retaining extensions 26 and 28 may be forced over the patient's teeth 27.1 and 27.2, the fastening means is opened and the tube 12 then slid along the length towards the patient's mouth until positioned. The fastening means is then allowed to close around the endotracheal tube 12, preventing relative movement of the endotracheal tube 12 and the retaining device 10. The retaining extensions 26 and 28 are secured over the patient's teeth. The endotracheal tube 12 is now immobilized in a desired position with respect to the patient. If it is desired to either insert the endotracheal tube 12 further into or partially remove from the patient's airway, then the fastening means can be released from the endotracheal tube 12. When the fastening means is open, the position of the endotracheal tube 12 in its longitudinal direction can be adjusted and guided by the clip 18.

A retaining device according to the present invention is easy to use because the retaining extensions 26 and 28, spaced-apart arms 22 and fastening means for resisting movement of a medical tube, can be combined as one device. The clamp 14 or fastening means can be operated with a single hand, so one person can readily adjust the retaining device.

Although the present invention has been substantially described with reference to the accompanying drawings and illustrated in detail, it is to be clearly understood that this is by way of illustration and example only, and is not to be taken by way of limitation. The spirit and scope of the invention are to be limited by the claims.

Thus, there is provided a medical tube retaining device that comprises a helpful means in all medical fields and applicable disciplines that is both cheaper and simpler to manufacture and offers performance advantages compared to conventional similar devices.

In yet another embodiment, the medical tube retaining device 10 has a first patient engaging portion 112 configured to engage a zone of an upper jaw of the patient, a second patient engaging portion 114 configured to engage a zone of a lower jaw of the patient. The first 112 and second 114 patient engaging portions are biased apart to provide a working gap 115 between them.

The medical tube guide means 14 is supported by the patient engaging portions 112 and 114 and is locatable relative to the patient engaging portions to guide the medical tube 12 through the working gap into the mouth of a patient.

In one embodiment, the first 112 and second 114 patient engaging portions are portions of a body having resiliently deformable portions (FIG. 1 and FIG. 2).

In another embodiment, the first 112 and second 114 patient engaging portions are in the form of a pair of arms having tooth-engaging portions (not shown).

In yet another embodiment, the first 112 and second 114 patient engaging portions are in the form of a pair of dental arches 116 having tooth engaging portions, The medical tube guide means 14 is sized to permit a view into the mouth of the patient (FIG. 1) through the working gap when the medical tube 12 is in place in the mouth of the patient.

Alternatively, the medical tube guide means 14 is located eccentrically the working gap. (FIGS. 1 and 2)

The medical tube guide means 14 is configured to immobilize the medical tube 12 in a desired position.

The medical tube guide means 14 includes securing means 117 operable between a securing and a releasing position, said securing means being configured to secure the medical tube 12 against longitudinal displacement unless the securing means 117 is in the releasing position in which case the medical tube 12 is longitudinally displaceable into and out of the mouth of the patient. The securing means is in the form of a clamp.

In an alternative arrangement, the pair of arms 22.1 and 22.2 meet at an apex or base 20. The apex or base 20 forms a support point for the medical tube 12, and the pair of arms 22.1 and 22.2 are pivotally displaceable relative to each other.

In another embodiment, the first 112 and second 114 patient engaging portions are biased apart by a one or more of resilient deformability of the material, a coil spring, a leaf spring, and fluid pressure, (not shown)

The medical tube guide means 14 may include an eye 19 through which the medical tube 12 to be guided passes.

The medical tube guide means 14 includes slip resistant portion (not shown) to inhibit the free movement of the medical tube 12 through the medical tube guide means 14.

In another embodiment, the first 112 and second 114 patient engaging portions include portions configured to approximate the bite size and dimensions of the patient.

The medical tube retaining device 10 can include two or more medical tube guide means. (not shown)

The invention claimed is:

1. A medical tube retaining device, said device including:
   a first patient engaging portion configured to engage a zone of an upper jaw of a patient, the first patient engaging portion being shaped in a form of a dental arch and having tooth engaging portions;
   a second patient engaging portion configured to engage a zone of a lower jaw of the patient, the second patient engaging portion being shaped in a form of a dental arch and having tooth engaging portions, the first and second patient engaging portions being biased apart to provide a working gap between
   wherein the first and second patient engagement portions meet at an apex, and are pivotably displaceable relative to one another; and
   a medical tube guide means for holding a medical tube located in an airway of the patient, the medical tube guide means being supportable on one or both of the patient engaging portions and located relative to the patient engaging portions such that in use the medical tube guide means is operatively positioned at the mouth of a patient in order to hold the medical tube as it exits the airway of the patient;
   wherein the medical tube guide means includes securing means operable between a securing and a releasing position, said securing means being configured to secure the medical tube against longitudinal displacement unless the securing means is in the releasing position in which case the medical tube is longitudinally displaceable into and out of the mouth of the patient, and
   wherein the medical tube guiding means further includes at least one bite block extending from at least one of the patient engaging portion for preventing a patient exerting a compressive force on the medical tube.

2. A medical tube retaining device as claimed in claim 1, wherein the first and second patient engaging portions are portions of a body having resiliently deformable portions.

3. A medical tube retaining device as claimed in claim 1, wherein the medical tube guide means is sized to permit a view into the mouth of the patient through the working gap when the medical tube is in place in the mouth of the patient.

4. A medical tube retaining device as claimed in claim 3, wherein the medical tube guide means is eccentrically located towards a commisure of the mouth.

5. A medical tube retaining device as claimed in claim 1, wherein the medical tube guide means is configured to immobilize the medical tube in a desired position.

6. A medical tube retaining device as claimed in claim 1, wherein the first and second patient engaging portions are biased apart by at least one of a resilient deformable material, a coil spring, a leaf spring, and fluid pressure.

7. A medical tube retaining device as claimed in claim 1, wherein the medical tube guide means includes an eye through which the medical tube to be guided passes.

8. A medical tube retaining device as claimed in claim 1, wherein the medical tube guide means includes a slip resilient portion to inhibit the free movement of the medical tube through the medical tube guide means.

9. A medical tube retaining device as claimed in claim 1, wherein the first and second patient engaging portions include portions configured to approximate a patient's bite size.

10. A method of reducing the risk of a patient biting closed a medical tube with which the patient is being intubated, said method including using a medical tube retaining device as claimed in claim 1 to bias a patient's teeth away from the medical tube while permitting the medical tube to be guided into an airway of the patient.

11. A medical tube retaining device, which comprises of:
a first patient engaging portion configured to engage a zone of an upper jaw of a patient, wherein the first patient engaging portion is shaped in a form of a dental arch and comprises of a resiliently deformable arm which is attached to a base on one end of the arm and is attached to a tooth engaging portion at the other end of the arm;
a second patient engaging portion configured to engage a zone of a lower jaw of the patient, wherein the second patient engaging portion is shaped in a form of a dental arch and comprises of a resiliently deformable arm which is attached to the base on one end of the arm and is attached to a tooth engaging portion at the other end of the arm; and
a medical tube guide means for holding a medical tube located in an airway of the patient, the medical tube guide means being supportable on one or both of the patient engaging portions and located relative to the patient engaging portions such that in use the medical tube guide means is operatively positioned at the mouth of a patient in order to hold the medical tube as it exits the airway of the patient.

12. A medical tube retaining device as claimed in claim 2, wherein the medical tube guide means is sized to permit a view into the mouth of the patient through the working gap when the medical tube is in place in the mouth of the patient; and wherein the medical tube guide means is located towards a side of the working gap.

* * * * *